United States Patent
Kita et al.

(10) Patent No.: US 8,644,450 B2
(45) Date of Patent: Feb. 4, 2014

(54) X-RAY FLUORESCENCE SPECTROMETER AND X-RAY FLUORESCENCE ANALYZING METHOD

(75) Inventors: Hiroaki Kita, Takatsuki (JP); Hiroshi Kobayashi, Takatsuki (JP)

(73) Assignee: Rigaku Corporation, Tokyo (JP)

( * ) Notice: Subject to any disclaimer, the term of this patent is extended or adjusted under 35 U.S.C. 154(b) by 0 days.

(21) Appl. No.: 13/807,896

(22) PCT Filed: Apr. 21, 2011

(86) PCT No.: PCT/JP2011/059797
§ 371 (c)(1),
(2), (4) Date: Dec. 31, 2012

(87) PCT Pub. No.: WO2012/002030
PCT Pub. Date: Jan. 5, 2012

(65) Prior Publication Data
US 2013/0101085 A1    Apr. 25, 2013

(30) Foreign Application Priority Data

Jul. 2, 2010 (JP) .................... 2010-151828

(51) Int. Cl.
*G01N 23/223* (2006.01)
(52) U.S. Cl.
USPC ............. 378/44; 378/45; 378/46; 378/49
(58) Field of Classification Search
None
See application file for complete search history.

(56) References Cited

U.S. PATENT DOCUMENTS

| 6,982,788 B2 * | 1/2006 | Hagler ............. 356/310 |
|---|---|---|
| 7,352,845 B2 | 4/2008 | Uda |
| 8,254,519 B2 | 8/2012 | Sugita et al. |
| 2006/0165218 A1 | 7/2006 | Uda |
| 2011/0007869 A1 * | 1/2011 | Gendreau et al. ............. 378/46 |
| 2011/0243299 A1 | 10/2011 | Sugita et al. |
| 2012/0281814 A1 * | 11/2012 | Yokhin et al. ............. 378/73 |

FOREIGN PATENT DOCUMENTS

| CN | 1823270 A | 8/2006 |
|---|---|---|
| CN | 101669024 A | 3/2010 |
| JP | 4-161844 A | 6/1992 |
| JP | 5-126768 A | 5/1993 |

(Continued)

OTHER PUBLICATIONS

International Preliminary Report on Patentability; PCT/JP2011/059797; Feb. 21, 2013.
Decision of Gran; Taiwan Patent Application No. 100123129; Nov. 23, 2012.
Decision of Grant; Korean Patent Application No. 10-2013-7002754; Mar. 29, 2013.
Office issued in Chinese Patent Application No. 201180031886.0 dated Jul. 5, 2013.

*Primary Examiner* — Hoon Song
*Assistant Examiner* — Danielle Fox
(74) *Attorney, Agent, or Firm* — Sughrue Mion, PLLC (57) ABSTRACT

The X-ray fluorescence spectrometer of the present invention includes a sample table (8) for a sample (S) having a crystalline structure, an X-ray source (1), a detecting unit (7) for detecting secondary X-rays (4) from the sample (S), a rotating unit (11) for rotating the sample table (8), a parallel translating unit (12) for causing the sample table (8) to undergo a parallel translational movement, a selecting unit (17) for selecting three of circumvent angles, at which diffracted X-rays can be circumvented, based on a diffraction profile obtained from the angle of rotation of the sample (S) and the intensity of secondary X-rays (4), the interval between the neighboring circumvent angles being smaller than 180°, and a control unit (15) for controlling the rotating unit (11) so as to set the sample (S) at the circumvent angle at which the sample table (8) will not interfere with any other structures.

4 Claims, 6 Drawing Sheets

(56) References Cited

FOREIGN PATENT DOCUMENTS

| | | |
|---|---|---|
| JP | 07-035708 A | 2/1995 |
| JP | 9-33459 A | 2/1997 |
| JP | 2613513 B2 | 2/1997 |
| JP | 9-304309 A | 11/1997 |
| JP | 1054811 A | 2/1998 |
| JP | 10-282022 A | 10/1998 |
| JP | 2001099791 A | 4/2001 |
| JP | 2001281177 A | 10/2001 |
| TW | 200634301 | 10/2006 |
| TW | 201012303 | 3/2010 |
| WO | 2008-107108 A1 | 9/2008 |

\* cited by examiner

X-RAY FLUORESCENCE SPECTROMETER AND X-RAY FLUORESCENCE ANALYZING METHOD

CROSS REFERENCE TO THE RELATED APPLICATION

This application is based on and claims Convention priority to Japanese patent application No. 2010-151828, filed Jul. 2, 2010, the entire disclosure of which is herein incorporated by reference as a part of this application.

BACKGROUND OF THE INVENTION

1. Field of the Invention

The present invention relates to an apparatus and a method both capable of accomplishing an accurate analysis, by minimizing an intensity of the diffracted X-rays incident on the detector, in the practice of the X-ray fluorescence analysis of a sample of a kind having a crystalline structure such as, for example, a monocrystal wafer (including, for example, a monocrystal silicon wafer and a monocrystal gallium arsenide wafer), which is used in the manufacture of semiconductor electronic circuit elements, and a monitor wafer formed by depositing, for example, electrode films over an entire measuring surface of a monocrystal silicon wafer.

2. Description of Related Art

Analysis of a surface layer of, for example, a silicon wafer has hitherto been carried out by irradiating a sample surface with primary X-rays and then detecting secondary X-rays emitted from the sample surface. Where with respect to a semiconductor substrate having electric wiring films made of aluminum (Al), silicon (Si) and copper (Cu) and deposited locally on a measuring surface of the monocrystal silicon wafer, the quality of each of those wiring films, for example, the film thickness and the content concentration are to be checked, an X-ray fluorescence spectrometer is generally utilized, which spectrometer is of a type designed to irradiate a sample, in the form of a monitor wafer having the wiring films deposited over the entire measuring surface of a monocrystal silicon wafer through the same process as the semiconductor substrate, with a primary ray and then to detect and analyze secondary X-rays emitted from the sample.

The X-ray fluorescence analyzing method has been suggested in the patent document 1, listed below, in which prior to the X-ray fluorescence analysis of a sample, the sample is irradiated with primary X-rays while the sample is rotated 180 degrees about a predetermined point on the sample, secondary X-rays including fluorescent X-rays and diffracted X-rays, both emitted from the sample; the sample is repositioned at a rotational direction position at which the resultant intensity of the secondary X-rays attains the minimum value; and under this condition, the sample is moved in XY directions perpendicular to each other in a plane parallel to a measuring surface of such sample, thereby accomplishing the analysis of the entire measuring surface of the sample.

Also, the total reflection X-ray fluorescence spectrometer has been suggested in the patent document 2, similarly listed below, which includes a sample table on which a sample having a crystalline structure is fixedly placed; an X-ray source for emitting primary X-rays towards the sample; a detector on which secondary X-rays emitted from the sample are incident; a parallel translating means for moving the sample table to an arbitrarily chosen position on the sample surface so as to allow the primary X-rays to irradiate; a rotary means for rotating the sample table about an axis perpendicular to the sample surface; and a control means for controlling the rotating means so that the sample may be set within an optimum rotational angle range of the sample determined by the theoretical calculation, in which range the total intensity of diffracted X-rays diffracted by the sample and then incident on the detector attains a value lower than a predetermined value.

3. Prior Art Literature

[Patent Document 1] JP Laid-open Patent Publication No. H05-126768

[Patent Document 2] JP Laid-open Patent Publication No. H10-282022

Figure 7:
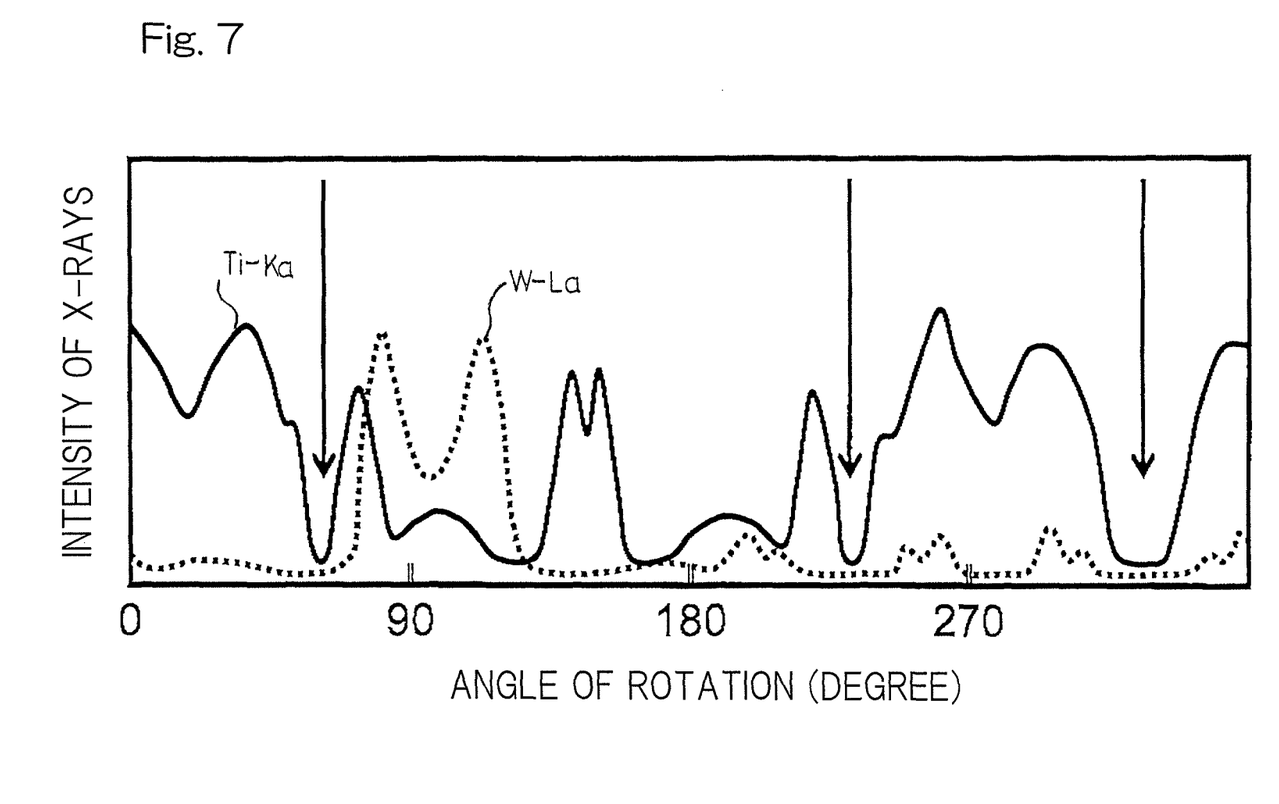
FIG. 7 is a diagram showing a diffraction profile exhibited by a sample having its crystalline structure that is not rotationally symmetric.

According to the patent document 1 listed above, since in the practice of the X-ray fluorescence analyzing method disclosed, the sample having the crystalline structure that has rotational symmetries through 180 degrees is measured, after the sample has been repositioned at the angle of rotation at which the intensity of the secondary X-rays attains the minimum value and a right half region of the sample has subsequently been measured, the sample is rotated to set a left half region of the sample to a right half region, thereby allowing the entire region of the sample to be measured. It has, however, been found that in this known method, two directions such as the angle of rotation of the sample, at which the intensity of the secondary X-rays attains the minimum value, and the angle, that is 180 degrees symmetric relative to that angle, are set and, therefore, any other angle than those two angles of rotation cannot be set. For this reason, in the case of the sample having the crystalline structure that has not rotational symmetries as shown in FIG. 7, no precise analysis is accomplished because the diffracted X-rays cannot be circumvented if the measurement is performed after the right half region of the sample has been measured and the sample has then been rotated 180 degrees to set the left half region of the sample to the right half region. Also, as the circumvent angle for circumventing diffracted X-rays, the angle at which the intensity of the secondary X-rays attains the minimum value is not necessarily the optimum angle and, therefore, no precise analysis can be accomplished as well.

According to the patent document 2 listed above, in the practice of the total reflection X-ray fluorescence spectrometer disclosed therein, the sample is set by means of the theoretical calculation to the optimum rotational angle range, within which the total intensity of the diffracted X-rays attains a value lower than the predetermined value. However, it has been found that a diffraction profile, detected actually by the spectrometer, and a diffraction profile theoretically calculated do not necessarily coincide with each other and, hence, no precise analysis can be accomplished. Here a diagram, in which the angle of rotation of the sample and the intensity of the secondary X-rays emitted from the sample at that angle of rotation are correlated with each other, is referred to as a diffraction profile.

SUMMARY OF THE INVENTION

In view of the foregoing, the present invention has been devised to substantially eliminate the problems and inconveniences inherent in the prior art method and apparatus discussed above and is intended to provide an X-ray fluorescence spectrometer and an X-ray fluorescence analyzing method, in which with a compact apparatus that does not require a large space for installation, a precise analysis can be accomplished with not only a sample having the crystalline structure, that is rotationally symmetric, but also a sample having the crystalline structure that is not rotationally symmetric.

In order to accomplish the foregoing objects, the present invention in accordance with one aspect thereof provides an X-ray fluorescence spectrometer which includes a sample table on which a sample having a crystalline structure is placed; an X-ray source for irradiating the sample with primary X-rays; a detecting unit for detecting secondary X-rays emitted from the sample; a rotating unit for rotating the sample table about an axis vertical to a sample measuring surface; a parallel translating unit for parallel translating the sample table to allow the primary X-rays to be directed to an arbitrarily chosen position of a half portion of the sample measuring surface while the rotating unit is halted; a control unit for storing a diffraction profile, in which the intensity of the secondary X-rays, emitted from the sample and incident on the detecting unit, and an angle of rotation of the sample are correlated with each other, by radiating the primary X-rays from the X-ray source, while the sample is rotated by the rotating unit an angle of 360 degrees about a predetermined point of the sample, and then displaying the diffraction profile by means of a display unit; and a selecting unit for allowing an attendant analyst to select at least three circumvent angles, at which diffracted X-rays can be circumvented, on the basis of the diffraction profile displayed by the display unit, the interval between the neighboring circumvent angles being smaller than 180 degrees; in which the control unit stores the circumvent angles, selected by the selecting unit, then reads out one of the stored circumvent angles, at which no interference occur between the sample table, the rotating unit and the parallel translating unit and any other structural component of the X-ray fluorescence spectrometer, in dependence on a point of measurement of the sample, and finally controls the rotating unit to set the sample at such circumvent angle that is read out.

According to the present invention, the attendant analyst can select at least three circumvent angles, at which the diffracted X-rays can be circumvented, the neighboring circumvent angles being spaced an angle smaller than 180 degrees from each other and the sample is set to one of the selected circumvent angles, at which the sample table, the rotating unit and the parallel translating unit will not interfere with any other structural component of the X-ray fluorescence spectrometer. Accordingly, with a compact apparatus that does not require a large space for installation, not only the sample of which the crystalline structure has rotational symmetries, but also the sample of which the crystalline structure has not rotational symmetries can be simply and accurately analyzed.

In a preferred embodiment of the present invention, the display unit employed in the X-ray fluorescence spectrometer displays a circumvent angle marking indicative of the position at the circumvent angle, selected by the selecting unit, together with the diffraction profile, stored in the control unit, and/or a measuring surface image of the sample. In this case, since the circumvent angle marking of the selected sample is displayed together with the diffraction profile and/or the measuring surface image of the sample, the attendant analyst can easily ascertain the selected circumvent angle position and whether or not the neighboring intervals are spaced an angle smaller than 180 degrees.

The present invention in accordance with another aspect thereof provides an X-ray fluorescence analyzing method that is practiced with the use of the X-ray fluorescence spectrometer of the kind referred to above, which method includes selecting at least three circumvent angles, at which diffracted X-rays can be circumvented, the interval between the neighboring circumvent angles being smaller than 180 degrees, and with respect to the sample set at the circumvent angle by the control unit, analyzing an entire measuring surface of the sample by moving the sample in a plane parallel to the measuring surface thereof.

According to the second aspect of the present invention, using a compact apparatus, not only the sample having the crystalline structure that is rotationally symmetric, but also the sample having the crystalline structure that is not rotationally symmetric can be simply and accurately analyzed.

In a preferred embodiment of the present invention, a circumvent angle marking indicative of the position at the circumvent angle, selected by the selecting unit, is displayed on the display unit together with the diffraction profile, stored in the control unit, and/or a measuring surface image of the sample. In this case, since the circumvent angle marking of the selected sample is displayed together with the diffraction profile and/or the measuring surface image of the sample, the attendant analyst can easily ascertain the selected circumvent angle position and whether or not the neighboring intervals are spaced an angle smaller than 180 degrees.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims.

In the accompanying drawings, like reference numerals are used to denote like parts throughout the several views, and.

DESCRIPTION OF PREFERRED EMBODIMENTS

Figure 1:
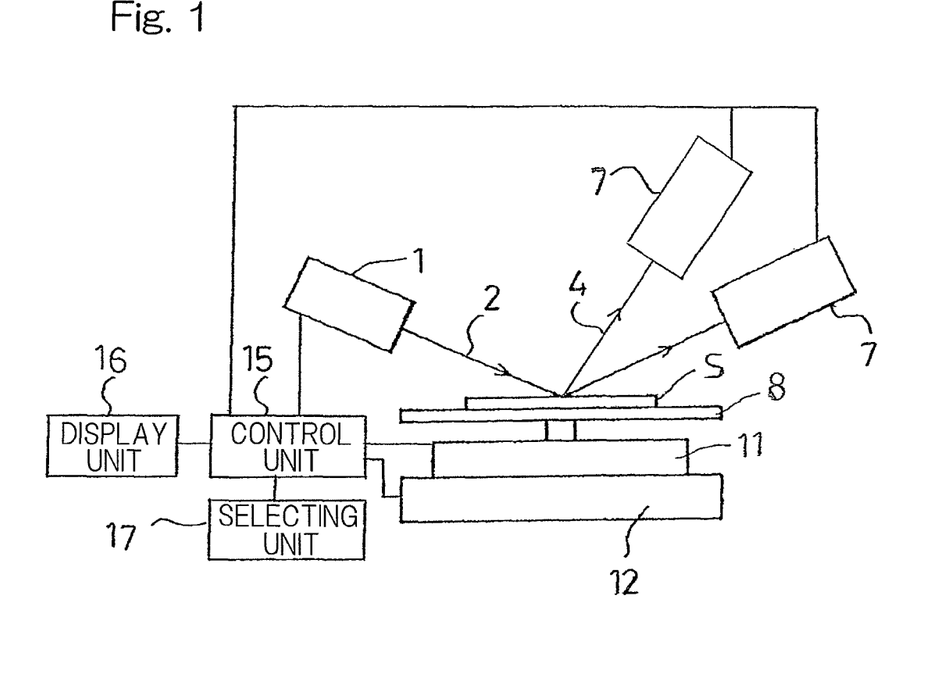
FIG. 1 is a schematic diagram showing an X-ray fluorescence spectrometer designed in accordance with a preferred embodiment of the present invention.

Hereinafter, an X-ray fluorescence spectrometer according to a preferred embodiment of the present invention will be described in detail. In the first place, the structure of the X-ray fluorescence spectrometer will be described with particular reference to the accompanying drawings. As best shown in FIG. 1, the X-ray fluorescence spectrometer includes an X-ray source 1 such as, for example, an X-ray tube for emitting primary X-rays 2 towards a sample S such as, for example, a monitor wafer, a detecting unit 7 for monochromating secondary X-rays 4, containing fluorescent X-rays and diffracted X-rays, both emitted from the sample S when the latter are irradiated with the primary X-rays 2, by means of a spectroscopic device such as, for example, LiF analyzing crystal and then detecting the intensity of the secondary X-rays 4, a sample table 8 on which the sample is placed, a rotating unit 11 for rotating the sample table 8 about an axis perpendicular to a measuring surface of the sample S, that is, about a center point O (See FIG. 2.) in the illustrated embodiment, and a parallel translating unit 12 for moving in XY directions perpendicular to each other in a plane parallel to a measuring surface of such sample so that in a condition with the rotating unit 11 rotatably supported, the primary X-rays 2 may be radiated onto an arbitrarily chosen position on the measuring surface of the sample S. The detecting unit 7 is in the form of a fixed type goniometer provided for each element to be measured.

Figure 2:
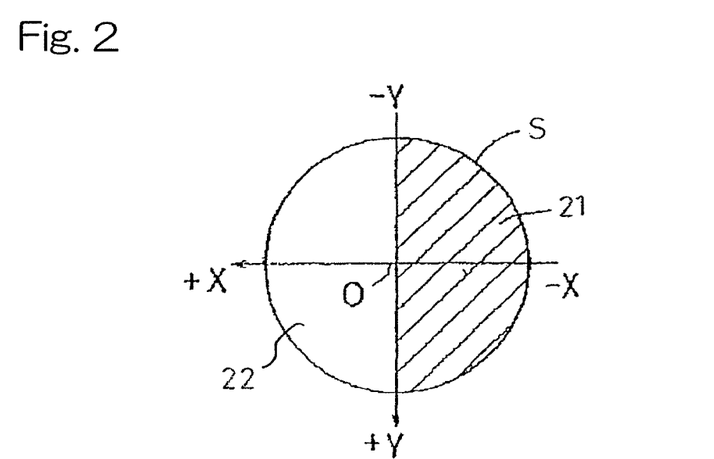
FIG. 2 is a diagram showing regions to which a sample can be translated parallel by the X-ray fluorescence spectrometer.

The stroke of the parallel translating unit 12 in one direction of an X direction and a Y direction is such as to be displaced at a stroke of a radius component, not a diametric component of the sample S. For example, where the point of irradiation of the primary X-rays 2 lies at the center point O of the sample S as shown in FIG. 2, by displacing the sample S in a +X direction and a Y direction by means of the parallel translating unit 12, it is possible for a desired point of measurement in a right half 21 (a region hatched) of the sample S to be displaced to the point of irradiation of the primary X-rays 2. Then, by displacing the center point O of the sample S to the point of irradiation of the primary X-rays 2 by means of the parallel translating unit 12, the sample S is rotated 180 degrees by means of the rotating unit 11, and the sample S is similarly displaced by means of the parallel translating unit 12 to thereby a desired point of measurement in a left half 22 (a region not hatched) of the sample S to the point of irradiation of the primary X-rays 2. In this way, in the X-ray fluorescence spectrometer of the present invention, the spectrometer can be compactized by limiting the displacement of the sample S in the X direction to the displacement of the sample S by a quantity equal to the radius component.

The X-ray fluorescence spectrometer according this embodiment of the present invention also includes a control unit 15, a display unit 16 and a selecting unit 17 shown in FIG. 1. The control unit 15 is operable to cause the X-ray source 1 to radiate the primary X-rays 2 while the sample S is rotated by the rotating unit 11 an angle of 360 degrees about the center point O of the sample S as viewed from top, to cause the display unit 16 to display a diffraction profile of a kind in which the intensity of the secondary X-rays (the diffracted X-ray) emitted from the sample S and incident upon the detecting unit 7 correlated with the angle of rotation of the sample S, and stores such diffraction profile. It is, however, to be noted that the direction of rotation of the sample S may be a counterclockwise direction as viewed from top.

Attendant analyst assigned to conduct the measurement selects at least three circumvent angles by the selecting unit 17, on the basis of the diffraction profile displayed on the display unit 16, the neighboring two of those three angles being spaced an angle of smaller than 180 degrees, at which the diffracted X-rays can be circumvented. Since the displacement of the sample S in the X direction is structurally limited to a radius component of the sample S for the purpose of compactization of the X-ray fluorescence spectrometer, the control unit controls the rotating unit 11 according to the position of a point of measurement of the sample S and then sets one of the selected at least three circumvent angles, at which the sample table 8, the rotating unit 11 and the parallel translating unit 12 will not interfere with any other structural component of the X-ray fluorescence spectrometer. The display unit 16 can also display a circumvent angle marking indicative of the circumvent angle of the sample S, which has been selected by the selecting unit 17, together with the diffraction profile, stored in the control unit 15, and/or a measuring surface image of the sample S.

Hereinafter, the X-ray fluorescence analyzing method, designed in accordance with another preferred embodiment of the present invention, will be described together with the operation of the X-ray fluorescence spectrometer according to the foregoing embodiment of the present invention. Prior to the start of the X-ray fluorescence analysis of the sample S, the diffraction profile for 360 degrees of the sample S is acquired.

Figure 3:
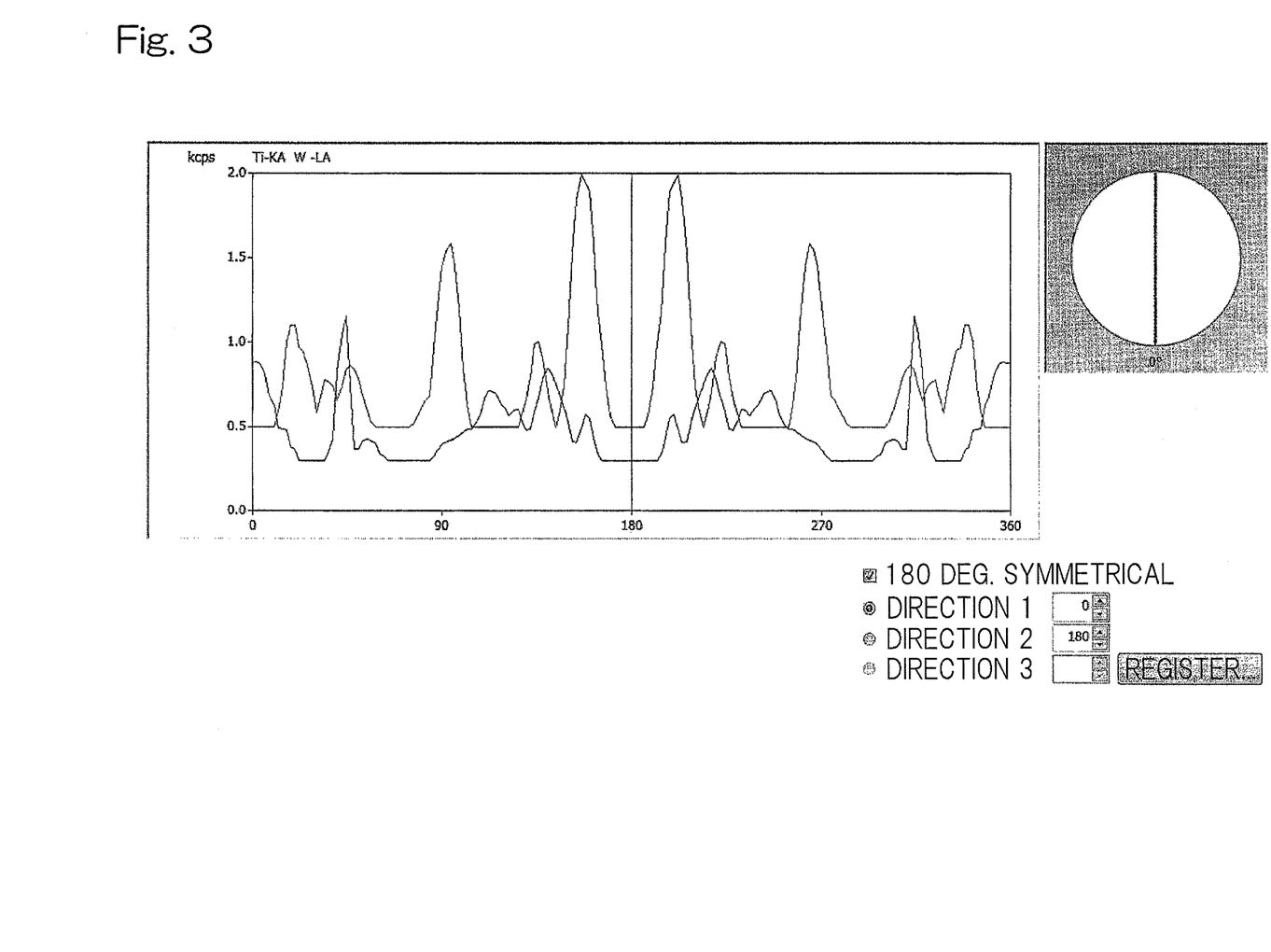
FIG. 3 is a diagram showing a diffraction profile of the sample measured by the X-ray fluorescence spectrometer.

In other words, the sample S is placed on the sample table 8, best shown in FIG. 1, and while the sample table 8 and the sample S are rotated by the rotating unit 11 an angle of 360 degrees about the center point O of the sample S, the sample S is irradiated with the primary X-rays 2 from the X-ray source 1 and the secondary X-rays 2 containing the fluorescent X-rays and the diffracted X-rays, both emitted from the sample S, is detected by the detecting unit 7. Thereby, the diffraction profile is stored in the control unit 15 and is displayed on the display unit 16 as shown in FIG. 3. Diffraction profiles of W-Lα line, measured by a fixed type goniometer for tungsten measurement purpose and W-Lα line measured by a fixed type goniometer for titanium measurement purpose are shown in FIG. 3.

Figure 4:
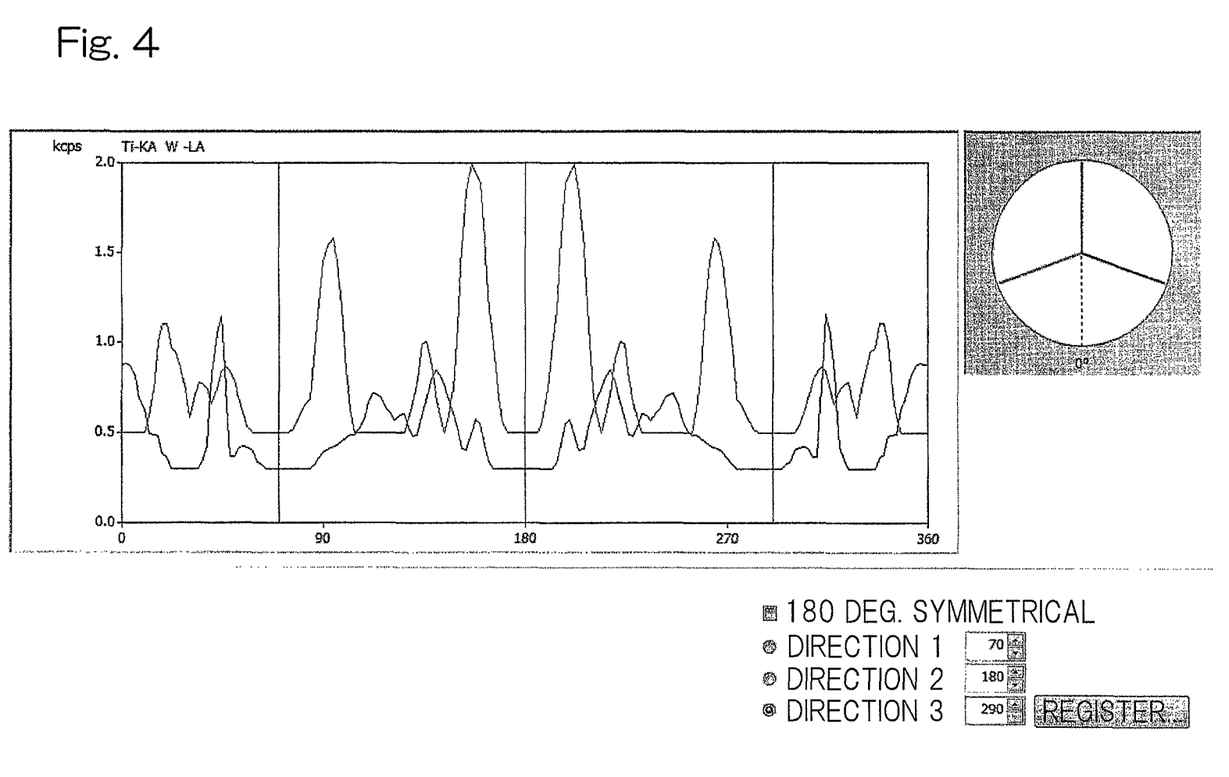
FIG. 4 is a diagram showing a screen image for setting the circumvent angle in the X-ray fluorescence spectrometer.

Thereafter, the attendant analyst selects a plurality of, for example, three circumvent angles, at which the diffracted X-rays can be circumvented and at which the intensity of the diffracted X-rays is low and no abrupt increase in intensity is exhibited at neighboring angular positions, out from the diffraction profiles shown in FIG. 4 illustrating a screen image for setting the circumvent angle displayed on the display unit 16. At this time, so that the interval between the neighboring circumvent angles selected may become smaller than 180 degrees, specific angles of 70 degrees, 180 degrees and 290 degrees, for example, are selected and the circumvent angles selected by the selecting unit 17 are registered as direction 1 (θ1), a direction 2 (θ2) and a direction (θ3), respectively. Once they are registered, the control unit 15 stores those circumvent angles as a measuring condition. Also, once they are registered, circumvent angle markings in the form of red colored vertical, blue colored and green colored vertical lines, respectively, are displayed on the display unit 16 at associated positions of the respective circumvent angles of 70 degrees, 180 degrees and 290 degrees on the diffraction profiles, as shown in FIG. 4, displayed on the display unit 16, and circumvent angle markings in the form of red colored, blue colored and green colored radii are displayed at the circumvent angles of 70 degrees, 180 degrees and 290 degrees on the measuring surface image, respectively. The circumvent angle markings may, however, be displayed on one or both of the diffraction profiles and the measuring surface image.

Since as described hereinabove the selected circumvent angle markings are displayed on the diffraction profile and/or the measuring surface image of the sample S, it can be easily ascertained visually whether or not the interval between the neighboring selected circumvent angles is smaller than 180 degrees. Also, if the neighboring circumvent angles are spaced more than 180 degrees, no registration can be made. Accordingly, the interval between the neighboring circumvent angles can be assuredly set to an angle smaller than 180 degrees. It is to be noted that the selected circumvent angles must be three or more in number. It is also to be noted that if the interval between the neighboring circumvent angles set to the angle of 180 degrees, the sample S is regarded as rotationally symmetric and it can be measured with the prior art method disclosed and previously discussed in connection with the patent document 1.

Figure 5:
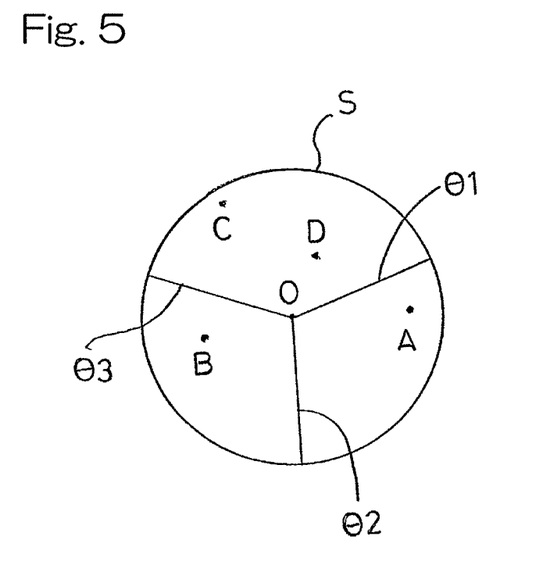
FIG. 5 is a diagram showing points of measurement in the sample that is measured by the X-ray fluorescence spectrometer.
Figure 6A:
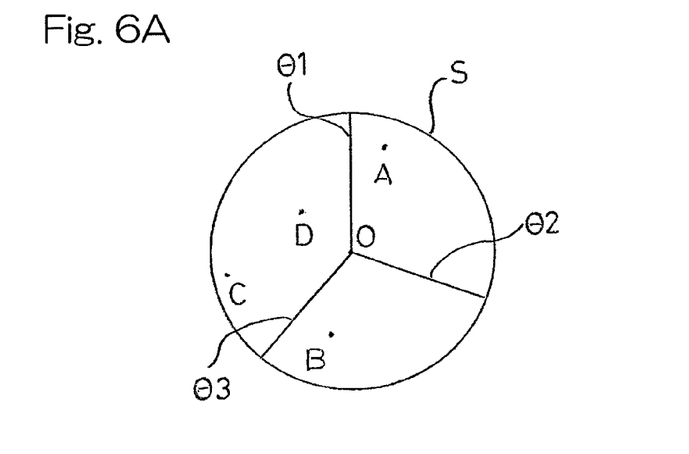
FIG. 6A is a diagram showing the sample set to a direction 1 of the circumvent angle in the X-ray fluorescence spectrometer.

Thereafter, upon start of the measurement of the points of measurement A, B, C and D of the sample S as shown in FIG. 5, the control unit 15 reads out the circumvent angle $\theta 1$ (70 degrees), which is registered in the direction 1, out from the circumvent angles stored in the measuring condition and then controls the rotating unit 11 to rotate the sample S to set the latter to the circumvent angle $\theta 1$ as shown in FIG. 6A. Accordingly, the sample S is set to the circumvent angle $\theta 1$ at which the diffracted X-rays can be circumvented. Subsequently, the parallel translating unit 12 is controlled by the control unit 15, the sample S is moved in the XY directions, and the point of measurement A is set to the point of irradiation of the primary X-rays 2. The primary X-rays 2 are irradiated upon the point of measurement A of the sample S and the secondary X-rays 4 emitted from the sample S is detected by the detecting unit 7. If the movement in the XY directions is effected in this way, the rotational direction position of the sample S does not change and the circumvent angle position is therefore maintained and, hence, influences resulting from noises brought about by the diffracted X-rays are eliminated with the S/N ratio consequently improved. Accordingly, even with a low content of an element, an accurate analysis can be achieved.

Figure 6B:
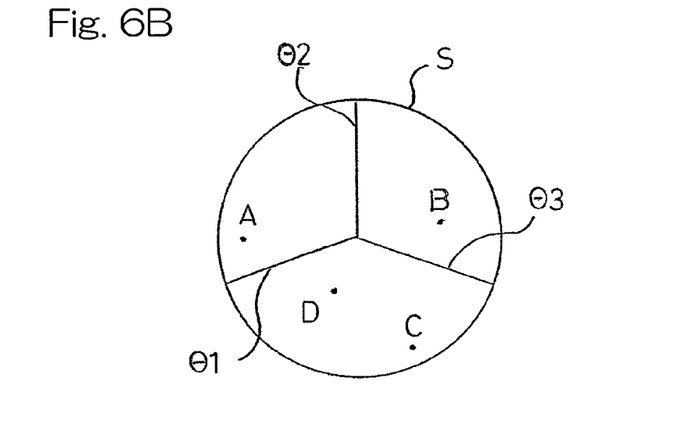
FIG. 6B is a diagram showing the sample set to a direction 2 of the circumvent angle in the X-ray fluorescence spectrometer.

Since at the circumvent angle $\theta 1$ shown in FIG. 6A, the subsequent point of measurement B lies in the left half of the sample S, no movement is accomplished with the parallel translating unit 12. For this reason, so that the sample table 8, the rotating unit 11 and the parallel translating unit 12 will not interfere with any other structural component of the X-ray fluorescence spectrometer of the present invention, the control unit 15 causes the parallel translating unit 12 to move the center point O of the sample S to the point of irradiation of the primary X-rays 2 and also causes the rotating unit 11 to rotate the sample S to the circumvent angle $\theta 2$ (180 degrees) of the direction 2, thereby setting it at the circumvent angle $\theta 2$ as shown in FIG. 6B. After that, the parallel translating unit 12 is controlled by the control unit 15, the sample S is moved in the XY directions and the point of measurement B is hence set to the point of irradiation of the primary X-rays 2. The primary X-rays 2 from the X-ray source 1 are irradiated upon the point of measurement B of the sample S and the secondary X-rays 4 emitted from the sample S are then detected by the detecting unit 7. Since the next point of measurement C lies in the right half of the sample S, in a manner similar to the point of measurement B the movement in the XY directions takes place by the parallel translating unit 12, followed by measurement.

Figure 6C:
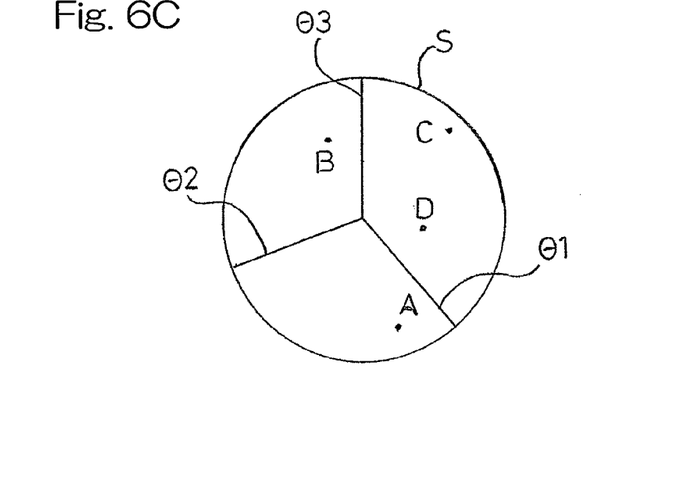
FIG. 6C is a diagram showing the sample set to a direction 3 of the circumvent angle in the X-ray fluorescence spectrometer.

Since at the circumvent angle $\theta 2$ shown in FIG. 6B, the next point of measurement D lies in the left half of the sample S, no movement is accomplished with the parallel translating unit 12. For this reason, so that the sample table 8, the rotating unit 11 and the parallel translating unit 12 will not interfere with any other structural component of the X-ray fluorescence spectrometer of the present invention, the control unit 15 causes the parallel translating unit 12 to move the center point O of the sample S to the point of irradiation of the primary X-rays 2 and also causes the rotating unit 11 to rotate the sample S to the circumvent angle $\theta 3$ (290 degrees) of the direction 3, thereby setting it at the circumvent angle $\theta 3$ as shown in FIG. 6C. After that, the parallel translating unit 12 is controlled by the control unit 15, the sample S is moved in the XY directions and the point of measurement D is hence set to the point of irradiation of the primary X-rays 2. The primary X-rays 2 from the X-ray source 1 are irradiated upon the point of measurement D of the sample S and the secondary X-rays 4 emitted from the sample S are then detected by the detecting unit 7.

Since as hereinabove described the circumvent angle, at which the diffracted X-rays can be circumvented, is stored as the measurement condition, in the event that the sample S having a similar crystalline structure is to be analyzed, the measurement can be done with the stored measurement condition read out and, with no need to select the circumvent angle, at which the diffracted X-rays can be circumvented for each sample S, the measurement can be accomplished simply and quickly. Also, as compared with the prior art technique in which the measurement is carried out in one direction and in a direction of rotational symmetry, the circumvent angle can be selected for each of analytical lines to be examined (for example, W-L$\alpha$ line, Ti-K$\alpha$ line and so on) and, therefore, the measurement can be accomplished at the circumvent angle at which the diffracted X-rays can be properly circumvented. Where the same circumvent angle is selected for all of those analytical lines to be examined, all of elements to be measured can be simultaneously measured at the same circumvent angle and, therefore, simultaneous multi-elements measurement with the diffracted X-rays being circumvented can be easily accomplished.

According to the X-ray fluorescence spectrometer or the X-ray fluorescence analyzing method, both designed in accordance with the present invention, with a compact apparatus that does not require a large space for installation, not only the sample having the crystalline structure that is rotationally symmetric, but the sample having the crystalline structure that is not rotationally symmetric can be simply and accurately analyzed.

Although the X-ray fluorescent spectrometer shown and described in connection with the preferred embodiment of the present invention has been referred as a wavelength dispersive X-ray fluorescence spectrometer of a simultaneous multi-elements type, it may be a wavelength dispersive X-ray fluorescent spectrometer of a type, in which a scanning type goniometer is employed, or an X-ray fluorescent spectrometer of an energy dispersive type. Also, the X-ray fluorescent spectrometer of the present invention may be an X-ray fluorescence spectrometer of a downward irradiating type or an X-ray fluorescence spectrometer of an upward irradiating type.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1 . . . X-ray source
2 . . . Primary X-rays
4 . . . Secondary X-rays
7 . . . Detecting unit
8 . . . Sample table
11 . . . Rotating unit
12 . . . Parallel translating unit 15 . . . Control unit
16 . . . Display unit
17 . . . Selecting unit
S . . . Sample

What is claimed is:

1. An X-ray fluorescence spectrometer which comprises:
a sample table on which a sample having a crystalline structure is placed;
an X-ray source for irradiating the sample with primary X-rays;
a detecting unit for detecting secondary X-rays emitted from the sample;
a rotating unit for rotating the sample table about an axis vertical to a sample measuring surface;
a parallel translating unit for parallel translating the sample table to allow the primary X-rays to be directed to an arbitrarily chosen position of a half portion of the sample measuring surface while the rotating unit is halted;
a control unit for storing a diffraction profile, in which the intensity of the secondary X-rays, emitted from the sample and incident on the detecting unit, and an angle of rotation of the sample are correlated with each other, by radiating the primary X-rays from the X-ray source, while the sample is rotated by the rotating unit an angle of 360 degrees about a predetermined point of the sample, and then displaying the diffraction profile by means of a display unit; and
a selecting unit for allowing an attendant analyst to select at least three circumvent angles, at which diffracted X-rays can be circumvented, on the basis of the diffraction profile displayed by the display unit, the interval between the neighboring circumvent angles being smaller than 180 degrees;
in which the control unit stores the circumvent angles, selected by the selecting unit, then reads out one of the stored circumvent angles, at which no interference occur between the sample table, the rotating unit and the parallel translating unit and any other structural component of the X-ray fluorescence spectrometer, in dependence on a point of measurement of the sample, and finally controls the rotating unit to set the sample at such circumvent angle that is read out.

2. The X-ray fluorescence spectrometer as claimed in claim 1, in which a circumvent angle marking indicative of the position at the circumvent angle, selected by the selecting unit, is displayed by the display unit together with the diffraction profile, stored in the control unit, and/or a measuring surface image of the sample.

3. An X-ray fluorescence analyzing method which comprises:
using the X-ray fluorescence spectrometer as defined in claim 1;
selecting at least three circumvent angles, at which diffracted X-rays can be circumvented, the interval between the neighboring circumvent angles being smaller than 180 degrees;
with respect to the sample set at the circumvent angle by the control unit, analyzing an entire measuring surface of the sample by moving the sample in a plane parallel to the measuring surface thereof.

4. The X-ray fluorescence analyzing method as claimed in claim 3, in which a circumvent angle marking indicative of the position at the circumvent angle, selected by the selecting unit, is displayed on the display unit together with the diffraction profile, stored in the control unit, and/or a measuring surface image of the sample.

* * * * *